United States Patent [19]

Zagorski et al.

[11] Patent Number: 4,576,153
[45] Date of Patent: Mar. 18, 1986

[54] BOWED UPPER ARM BRACE

[76] Inventors: Joseph Zagorski, 355 Marquesa Dr., Coral Gables, Fla. 33156; Alan Finnieston, 2480 W. 82nd St., Hialeah, Fla. 33016

[21] Appl. No.: 579,543
[22] Filed: Feb. 13, 1984
[51] Int. Cl.$^4$ .............................................. A61F 5/04
[52] U.S. Cl. .............................................. 128/87 R
[58] Field of Search ............... 128/89 R, 87 R, 90, 128/165

[56] References Cited

U.S. PATENT DOCUMENTS

| 2,682,869 | 7/1954 | Papp | 128/87 R |
| 4,436,088 | 3/1984 | Finnieston | 128/90 |

FOREIGN PATENT DOCUMENTS 102439  4/1899  Fed. Rep. of Germany ..... 128/80 J

*Primary Examiner*—John D. Yasko
*Attorney, Agent, or Firm*—Larson and Taylor

[57] ABSTRACT

An upper arm brace for maintaining broken bone segments in a proper healing orientation by protecting and reinforcing the surfaces of the upper arm of the wearer between the shoulder zone and elbow zone is disclosed. The brace includes an elongate, generally U-shaped posterior member. The sidewalls of the posterior member are bowed inwardly toward the body of the wearer. The upper arm brace also includes an elongate generally C-shaped anterior member which extends around the interior surface of the upper arm. The side walls of the anterior member are similarly bowed inwardly to mate with the sidewalls of the posterior member. Both the anterior and posterior members are made of a semi-rigid material with the respective sidewalls being capable of being flexed. With this construction, the anterior and posterior members come together to encase the upper arm tightly so that the broken bone fragments are held by the soft tissue in a proper, slightly valgus, healing orientation. Preferably, the anterior member has a central bulged portion to accommodate the biceps muscle and to assist in retaining the arm brace in a predetermined desired position.

5 Claims, 6 Drawing Figures

BOWED UPPER ARM BRACE

FIELD OF THE INVENTION

The present invention relates generally to a brace for maintaining broken bone segments in a proper healing orientation, and more particularly to an upper arm brace which holds broken bone fragments in a proper, slightly valgus healing orientation.

BACKGROUND OF THE INVENTION

Numerous devices have been disclosed in the prior art for maintaining broken bone segments of the upper arm in a fixed, healing position. The most common type of device is the well known plaster cast. In addition, various braces have also been proposed, including various semi-rigid braces.

When using a plaster cast on the upper arm, it is the usual procedure to put the cast along the length of the arm with the arm bent at the elbow. When this occurs, the arm hangs from the shoulder so that the weight of the cast and arm must be supported. This support is provided by a collar and cuff. As the collar and cuff support the weight of the cast, the point of attachment of the cuff to the cast determines how the bone segments angulate relative to one another. With no support, there is a strong tendency for the bone segments to angulate. Therefore, by changing the point of attachment of the cuff along the length of the lower arm, the tendency of the bones to angulate coin be overcome.

Rather than trying to have the bone segments not angulate at all, the angulation into valgus is generally desired because the broken bone segments are usually still connected along the exterior side by soft tissues. On the interior side, there is usually a breakage of the corresponding soft tissue connection so that there is a latent tendency of the bone to again move into a varus orientation. Therefore, by urging the bone segments into a valgus orientation, the tendency of the bone segments into a varus orientation is compensated for. In addition, the valgus orientation actually helps urge the proximal ends of the bone segments into contact with one another against the pull of the soft tissue connecting the exterior sides of the bone segments.

In using a plaster cast, the cast is left in place and supported by the collar and cuff for several weeks. During this time, the arm and shoulder are immobilized. This usually results in several weeks of rehabilitation. Obviously, this long time period for rehabilitation is undesired.

When applying a plaster cast to broken bone segments in the limb, it is known to shape the plaster cast so that a slight pressure is present on the same side of the bone break where the soft tissue has broken away from the bone. In this manner, the fracture site is urged toward the soft tissue which is unbroken on the other side of the break. Such a cast is shaped so that there are essentially three points of force applied against the bone, forces on either end of the bone pushing against the side of the bone where the soft tissue is still connected, and the force located at the break in the bone pushing in the opposite direction toward the connected soft tissue. This is referred to as "three point fixation".

SUMMARY OF THE INVENTION

In accordance with the present invention, a bowed upper arm brace for maintaining the broken bone segments in a proper healing orientation by protecting and reinforcing the surfaces of the upper arm of the wearer between the shoulder zone and the elbow zone is provided. This upper arm brace attempts to provide "three points of fixation" so that a slight valgus force is applied to the broken bone segments during fracture healing. The upper arm brace includes an elongate, generally U-shaped posterior member. The posterior member has a base and sidewalls extending around the posterior surface of the upper arm. These sidewalls are bowed inwardly toward the body of the user. An elongate generally C-shaped anterior member is disposed in overlapping relationship with the longitudinal side edges of the posterior member. The anterior member has a base and sidewalls extending around the anterior surface of the upper arm with the sidewalls being bowed inwardly to mate with the sidewalls of the posterior member. The anterior and posterior members are made of a semi-rigid material so that the sidewalls of the members are capable of being flexed somewhat. The anterior and posterior members encase the upper arm with the inner surfaces of the anterior and posterior members being in contact with the surface of the upper arm so that the bone fragments are held in the proper orientation.

In the preferred embodiment of the present invention, the base of the anterior member includes a central portion which is bulged outwardly to accommodate the biceps muscle. The engagement of the outwardly bulged central portion with the biceps muscle assists in retaining the arm brace in the predetermined desired position on the upper arm. The upper arm brace also includes fastening means on the posterior member for securing the posterior and anterior members snuggly together.

In accordance with the present invention, the anterior and posterior members are made of a molded structure of plastic material with a plurality of vent holes therein. The anterior member also includes an inside surface of perforated foam material. The lower edge of the base of the posterior member is also extended beyond the sidewalls of the posterior members to cover the posterior portion of the arm immediately above the elbow and the lower edge of the base of the anterior member is curved upwardly to form a recessed portion received in the crotch between the upper arm and forearm of the user.

It is an object of the present invention to provide an upper arm brace wherein the base of a posterior segment applies pressure to the flesh on the posterior side of the arm to exert a stabilizing support to the upper arm. In addition, an anterior segment is also provided which is provided with a contoured surface to apply pressure to the flesh over the biceps of the wearer.

It is also an object of the present invention to provide an upper arm brace wherein the upper end of the arm brace adjacent the armpit is cut away to allow the arm to reach a maximum height at the outer shoulder and to rest comfortably under the armpit. This allows for maximum comfort, protection, and some limited mobility.

It is a further object of the present invention to provide an upper arm brace with a liner provided along the anterior segment which acts as a padding along the biceps of the user.

Still another object of the present invention is to maintain the broken bone segments in "three points of fixation" so that a slight valgus angulation force of the bone segments is provided by use of bowed sidewalls.

Other objects, features, and advantages of the present invention are stated in or apparent from a detailed description of a presently preferred embodiment of the invention found hereinbelow.

DETAILED DESCRIPTION OF THE PREFERRED EMBODIMENT

With reference now to the drawings in which like numerals represent like elements throughout the several views, a bowed upper arm brace 10 according to the present invention for the left arm is depicted in FIGS. 1 to 4. Bowed upper arm brace 10 is similar to the upper arm brace disclosed in applicant's prior pending application Ser. No. 299,815 entitled "Upper Arm Brace" and filed on Sept. 8, 1981. This prior application is herein incorporated by reference.

Upper arm brace 10 includes an anterior member 12 and a posterior member 14. As shown in drawings, anterior member 12 is partially received in posterior member 14 so that anterior member 12 and posterior member 14 are slidable with respect to each other. In particular, as shown best in FIG. 3, anterior member 12 and posterior member 14 are slidable vertically with respect to each other so as to accommodate larger or smaller girths of arms therebetween. In this manner, upper arm brace 10 generally accommodates all sized arms.

Figure 3:
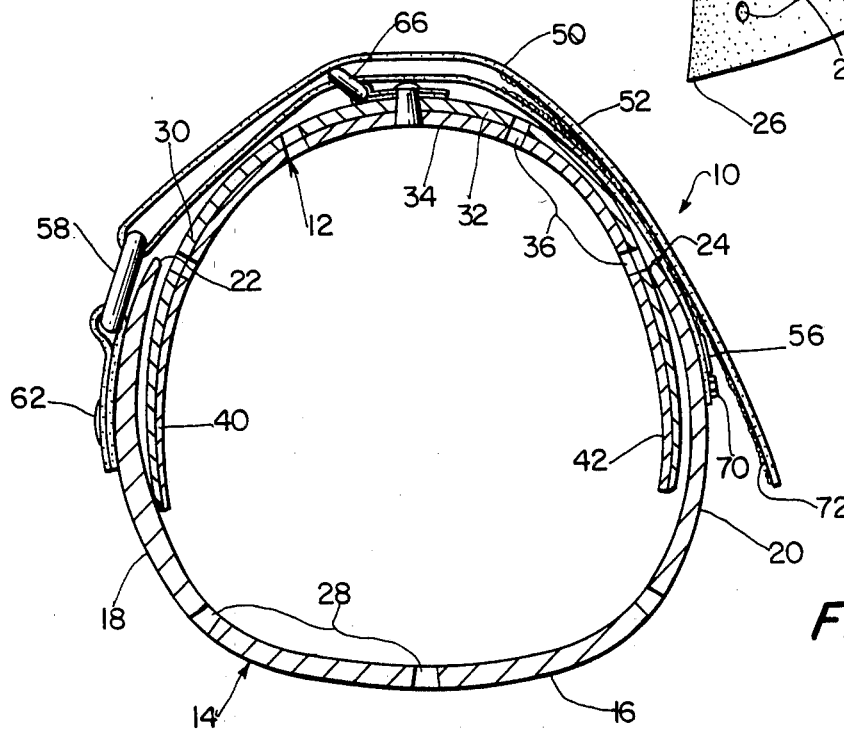
FIG. 3 is a cross-sectional view of the upper arm brace depicted in FIG. 1 taken along the line 3—3.

As shown best in FIG. 3, posterior member 14 is generally U-shaped in cross section and is preferably provided with a length of approximately six to eight inches. Posterior member 14 includes a base 16 which is generally flat and sidewalls 18 and 20 which are curved upwardly from base 16 and have upper terminal ends 22 and 24, respectively. As shown best in FIG. 1, sidewalls 18 and 20 are slightly bowed along the longitudinal axis of upper arm brace 10 for a reason to be described subsequently. It should also be noted that end 26 of base 16 is extended beyond the ends of sidewalls 18 and 20 to provide protection for the back of the arm immediately above the elbow.

Posterior member 14 is preferably made of a plastic material which is substantially rigid. However, as base 16 and sidewalls 18 and 20 are relatively thin, some flexibility is provided between upper ends 22 and 24. In this manner, upper ends 22 and 24 can be flexed or expanded by hinged movement of sidewalls 18 or 20 relative to base 16. Posterior member 14 is perforated by a plurality of holes 28 which are arranged in a pattern.

Anterior member 12 is generally U-shaped with somewhat more rounded or curved corners than posterior member 14. For this reason, anterior member 12 is more appropriately considered as generally C-shaped. Anterior member 12 includes an outside surface 30 and an inside surface 32. Inside surface 32 is lined with a foam material 34. A plurality of holes 36 are provided in anterior member 12 in a suitable pattern.

Figure 1:
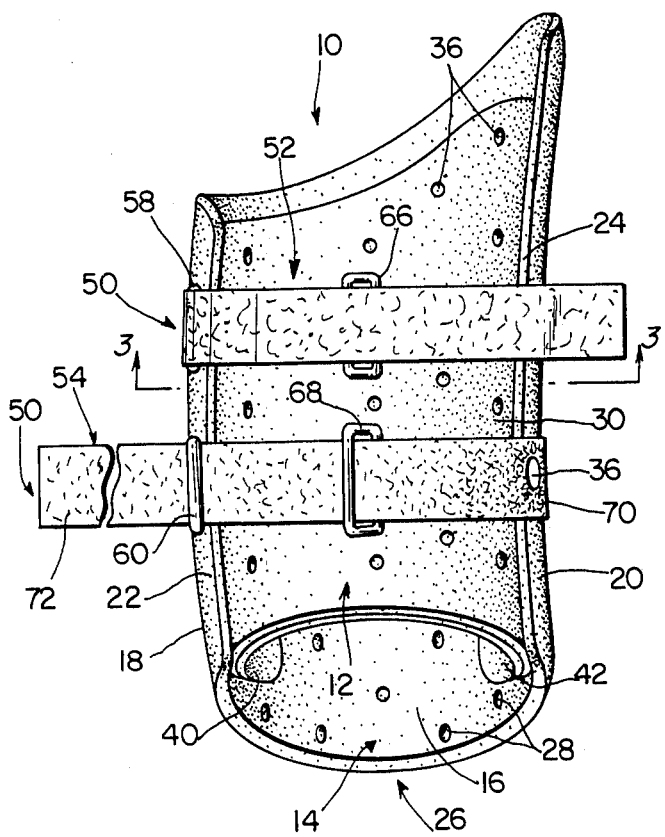
FIG. 1 is a front elevation view of a bowed upper arm brace for the left arm according to the present invention.
Figure 2:
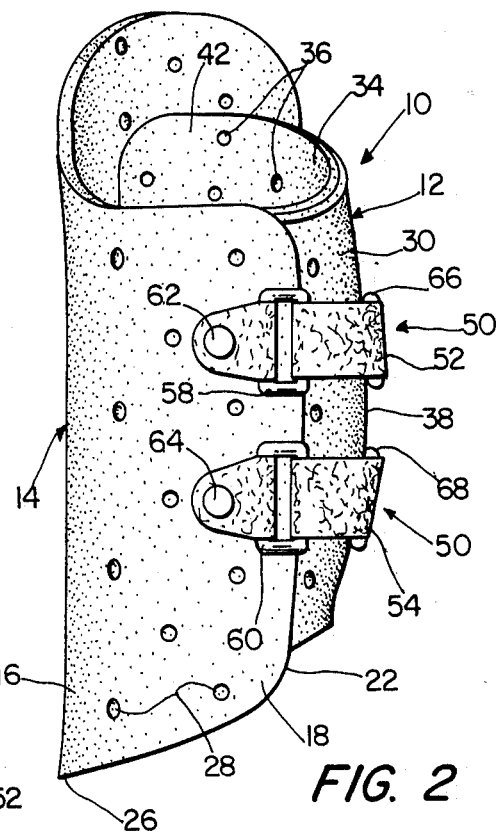
FIG. 2 is a side elevation view of the upper arm brace 10 depicted in FIG. 1.
Figure 4:
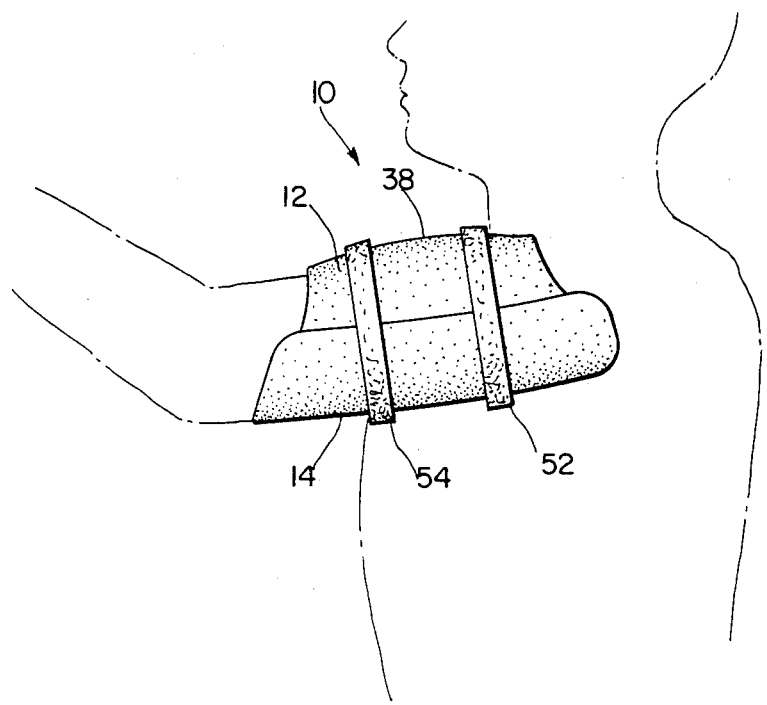
FIG. 4 is a side elevation view showing the upper arm brace depicted in FIG. 1 on the arm of a wearer.

As shown best in FIGS. 2 and 4, anterior member 12 includes a bulged portion 38 in the center thereof. Bulged portion 38 is sized to engage the biceps muscle of the wearer. Anterior member 12 also includes sidewalls 40 and 42 which are bowed complementary to sidewalls 18 and 20 of posterior member 14. As with posterior member 14, anterior member 12 is made of a relatively rigid plastic material which is of a thickness so that some flexibility of sidewalls 40 and 42 is allowed.

As depicted in FIG. 4, anterior member 12 fits over the biceps muscle of the wearer while base 16 of posterior member 14 overlays the muscle along the rear of the wearer's arm. In order to maintain upper arm brace 10 in position, a keeper means 50 is provided. In this embodiment, keeper means 50 includes straps 52 and 54. Each strap 52 and 54 is attached at one end to sidewall 20 such as by rivet 56 as shown. On the other sidewall 22, straps 52 and 54 pass through a respective buckle 58 and 60. Buckles 58 and 60 are attached to sidewalls 22 by rivets 62 and 64, respectively.

Located on anterior member 12 on either longitudinal side of bulged portion 38 are buckles 66 and 68. Respective straps 52 and 54 pass through buckles 66 and 68 as straps 52 and 54 extend from sidewall 20 to sidewall 22 as shown best in FIG. 1 with respect to strap 54. Upon reversing direction as shown by strap 52 in FIG. 1, straps 52 and 54 pass over buckles 66 and 68 and are removably secured adjacent sidewall 20. Preferably, straps 52 and 54 are Velco-type straps having a portion adjacent one end which comprises J-hooks such as portion 70 and a second portion 72 provided with loops which are releasably captured by the J-hooks. With this construction, straps 52 and 54 are adjustably attached to themselves. By pulling on the free ends of straps 52 and 54, the pressure exerted on anterior member 12 is adjustable. It should be appreciated that the arrangement of buckles 66 and 68 with straps 52 and 54 maintains anterior member 12 substantially longitudinally in place with respect to posterior member 14.

Figure 5:
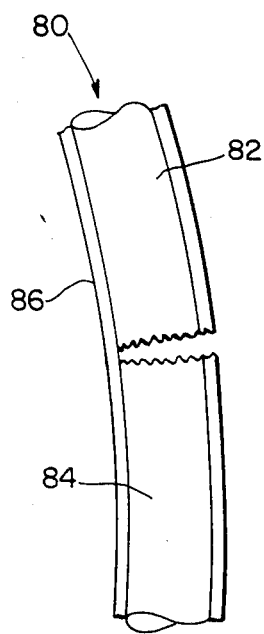
FIG. 5 is a schematic front elevation view of a broken bone.

Depicted in FIG. 5 is a broken bone 80 including bone segments 82 and 84 extending on either side of the break. Located around and along the length of the bone 80 is soft tissue 86. As shown, soft tissue 86 has separated on bone segments 82 and 84 at the outer or most open part of the break. However, at the inner part of the break, soft tissue 86 is still connected along the longitudinal length of bone 80. This break in bone 90 and soft tissue 86 is typical of an upper arm break on which bowed upper arm brace 10 is used.

Figure 6:
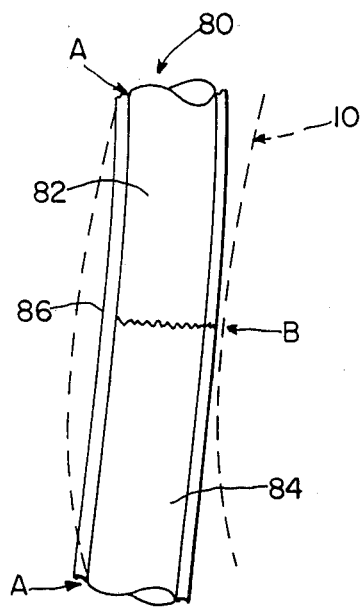
FIG. 6 is a schematic front elevation view of the broken bone depicted in FIG. 5 in a proper healing orientation.

Depicted in FIG. 6 is bone 80 which is being maintained in a proper healing orientation. Initially, bone 80 was in a varus angulation with the body of the user on the left hand side of bone 80 as depicted in FIG. 5. Due to the location of the body of the user on the left hand side of bone 80, and in particular with obese patients, there is a tendency for the body to continually press against the break in bone 80 so that bone 80 is continually urged to angulate in the varus direction. For this reason, upper arm brace 10 is used as depicted in FIG. 6 in phanthom. With upper arm brace 10, "three points of fixation" are used to assist in maintaining bone 80 in an acceptable healing orientation.

As shown in FIG. 6, upper arm brace 10 exerts fixing forces A at the upper and lower ends of upper brace 10 which are directed laterally away from the body of the user. Upper arm brace 10 also exerts a fixing force B at the approximate location of the break laterally toward the body of the user. In this manner, upper arm brace 10 assists in providing an acceptable healing orientation which is slightly valgus and which resists the natural tendency of the body to move bone 80 to a slightly varus orientation. It should be appreciated that upper arm brace 10 provides fixing forces A and B which tend to bring the separated portions of soft tissue 86 together on one side of bone 80 and to separate the connected soft tissue 86 on the other side of bone 80. However, the portion of soft tissue 86 which has not be separated is sufficiently strong to resist the separating forces so that bone 80 is aligned in an acceptable orientation by upper arm brace 10.

In use, upper arm brace 10 functions in the following manner. Initially, bone 80 is aligned by the physician into the proper healing orientation. Next, anterior member 12 is placed over the biceps muscle of the arm of the wearer and posterior member 14 is placed along the rear of the arm of the wearer. This is done by separating anterior member 12 and posterior 14 and joining them about the arm of the user, or by loosening straps 52 and 54 of upper arm brace 10 whereby anterior member 12 and posterior member 14 are separated sufficiently so that upper arm brace 10 can be slid along the arm of the user to the proper position. In any event, once anterior member 12 and posterior member 14 are arranged on the arm of the user, straps 52 and 54 are tightened. This is accomplished by pulling on straps 52 and 54 as straps 52 and 54 extend from sidewall 20 to sidewall 18 such as depicted by strap 54 in FIG. 1. In order to keep straps 52 and 54 in the tightened condition, straps 52 and 54 are doubled back on one another, respectively, such as shown by strap 52 in FIG. 1. This causes J-hook portion 70 to engage loop portion 72 so that straps 52 and 54 are securely held in place.

With use of upper arm brace 10, the arm of the wearer is placed in a sling for approximately two weeks. During this time, the wearer can gently exercise the arm as healing progresses. After two weeks, the sling is removed and the upper arm brace left in place for another eight to twelve weeks. During this subsequent period of time, the arm is continually exercised. Therefore, when upper arm brace 10 is fully removed, little or no rehabilitation is necessary to restore mobility.

While upper arm brace 10 has been depicted as an arm brace for the left arm, it should be appreciated that a complimentary shaped upper arm brace is used for the right arm.

Although the present invention has been described with respect to an exemplary embodiment thereof, it will be understood by those of ordinary skill in the art that variations and modifications can be effected within the scope and spirit of the invention.

We claim:

1. An upper arm brace for maintaining broken bones segments in an acceptable healing orientation by protecting and reinforcing the surfaces of the upper arm of the wearer between the shoulder zone and the elbow zone, said brace comprising:

an elongate, generally U-shaped posterior member having a base and sidewalls extending around the posterior surface of the upper arm, said sidewalls being bowed inwardly toward the body of the wearer; and an elongate generally C-shaped anterior member having a base and sidewalls extending around the anterior surface of the upper arm, said sidewalls being bowed inwardly to mate with the sidewalls of said posterior member with the longitudinal side edges of said anterior member being disposed in overlapping relationship with the longitudinal side edges of said posterior member whereby said anterior and posterior members encase the upper arm with the inner surfaces of said anterior and posterior members being in contact with the surface of the upper arm;

said anterior and posterior members being made of a semirigid material with said sidewalls of said members capable of being flexed whereby said broken bone fragments are urged toward an acceptable healing orientation by a slight valgus force.

2. An upper arm brace as claimed in claim 1 wherein said base of said anterior member has a central portion bulged outwardly to accommodate the biceps muscle whereby the engagement of the outwardly bulged central portion of said anterior member with the biceps muscle assists in retaining the arm brace in a predetermined desired position on the upper arm.

3. An upper arm brace as claimed in claim 2 and further including fastener means mounted on said posterior member for securing said posterior and anterior members snugly together in overlapping relationship.

4. An upper arm brace as claimed in claim 2 wherein said members comprise a molded structure of plastic material including a plurality of holes therein arranged in a venting pattern, and wherein said anterior member includes an inside surface of perforated foam material.

5. An upper arm brace according to claim 2 wherein the lower edge of said base of said posterior member is extended beyond said side walls of said posterior member to cover the posterior portion of the arm immediately above the elbow, and the lower edge of said base of said anterior member is curged upwardly to form a recessed portion received in the crotch between the arm and forearm of the wearer.

* * * * *